(12) United States Patent
Vicari et al.

(10) Patent No.: US 9,290,384 B2
(45) Date of Patent: Mar. 22, 2016

(54) PROCESS FOR PREPARING ACETYLENE AND SYNTHESIS GAS

(71) Applicant: BASF SE, Ludwigshafen (DE)

(72) Inventors: Maximilian Vicari, Limburgerhof (DE); Christian Weichert, Bad Duerkheim (DE); Dirk Grossschmidt, Mannheim (DE); Michael Russ, Roemerberg (DE); Mirko Haider, Maxdorf (DE); Horst Neuhauser, Dudenhofen (DE); Michael L. Hayes, Gonzales, LA (US)

(73) Assignee: BASF SE, Ludwigshafen (DE)

( * ) Notice: Subject to any disclaimer, the term of this patent is extended or adjusted under 35 U.S.C. 154(b) by 516 days.

(21) Appl. No.: 13/902,175

(22) Filed: May 24, 2013

(65) Prior Publication Data

US 2013/0334464 A1 Dec. 19, 2013

Related U.S. Application Data

(60) Provisional application No. 61/659,446, filed on Jun. 14, 2012.

(51) Int. Cl.
*C01B 3/38* (2006.01)
*C01B 3/24* (2006.01)
*C01B 3/36* (2006.01)

(52) U.S. Cl.
CPC ........................................ *C01B 3/36* (2013.01)

(58) Field of Classification Search
CPC ........................................................ C01B 3/36
See application file for complete search history.

(56) References Cited

U.S. PATENT DOCUMENTS

| 5,824,834 A | 10/1998 | Bachtler et al. |
| 2012/0022308 A1 | 1/2012 | Koenigsmann et al. |
| 2012/0119149 A1 | 5/2012 | Russ et al. |
| 2012/0119150 A1 | 5/2012 | Grossschmidt et al. |

FOREIGN PATENT DOCUMENTS

| WO | WO 2012/010508 A1 | 1/2012 |
| WO | WO 2012/062584 A1 | 5/2012 |
| WO | WO 2012/062784 A1 | 5/2012 |

OTHER PUBLICATIONS

Ullmann's Encyclopedia of Industrial Chemistry, 1985, 5$^{th}$ Edition, vol. A1, 52 pages.

*Primary Examiner* — Melvin C Mayes
*Assistant Examiner* — Kenneth Vaden
(74) *Attorney, Agent, or Firm* — Oblon, Spivak, McClelland, Maier & Neustadt, L.L.P.

(57) ABSTRACT

A process for preparing acetylene and synthesis gas by partial oxidation of hydrocarbons with oxygen, is disclosed. The process consists of separately preheating and then mixing a first input stream containing a hydrocarbon and a second input stream containing oxygen, supplying the first input stream and the second input stream via a burner block to a firing space, quenching a cracking gas obtained to produce a process water stream and a product gas stream, cooling the product gas stream in a cooling column by direct heat exchange with cooling water, depleting soot in an electrostatic filter, combining all process water streams and passing through soot channels, subjecting the combined process water stream to a cleaning operation by partial vaporization in a one-stage flash vessel to obtain a cleaned process water stream, and recycling the cleaned process water stream into the process.

20 Claims, 2 Drawing Sheets

PROCESS FOR PREPARING ACETYLENE AND SYNTHESIS GAS

Figure 1:
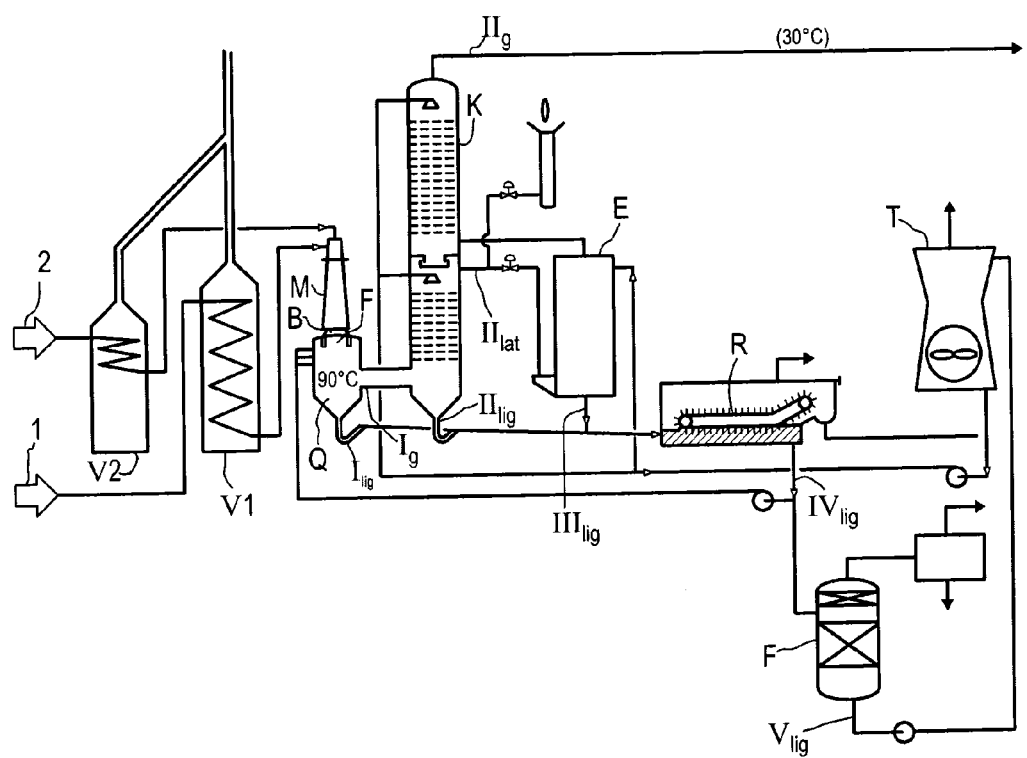

The present invention relates to a process for preparing acetylene and synthesis gas by partial oxidation of hydrocarbons with oxygen.

The above partial oxidation is a high-temperature reaction which is typically conducted in a reactor system comprising a mixing unit, a burner block and a quench unit, and is described, for example, in Ullmanns Encyclopedia of Industrial Chemistry (5th Edition, Volume A1, pages 97-144) or US 005824834A.

According to Ullmanns Encyclopedia of Industrial Chemistry (5th Edition, Volume A1, pages 97-144), the feedstocks are heated separately in preheaters. The heated feedstocks are mixed in a mixing unit and supplied via a mixing diffuser to a burner and further to a firing space. Downstream of the firing space, nozzles are used to supply an aqueous quench medium to the cracking gas, which is cooled rapidly to about 80-90° C. Through suitable selection of the oxygen ratio $\lambda$ ($\lambda<0.31$), the oxygen ratio $\lambda$ being understood to mean the ratio of the amount of oxygen actually present in the second input stream to the stoichiometrically necessary amount of oxygen, the process is conducted such that the yield of acetylene based on the dry cracking gas is at an optimum (>8%). In this context, oxygen ratio $\lambda$, as usual, is understood to mean the ratio of the amount of oxygen actually present to the stoichiometrically necessary amount of oxygen required for the full combustion of the feedstocks. In this case, however, the soot loading of the cracking gas is also at a maximum. The soot formed from the gas phase in the firing space is partly precipitated by the quench, in a downstream cooling column and a downstream electrostatic filter. The product gas stream containing products of value is removed separately via the cooling column. Downstream of the electrostatic filter, the soot concentration in the remaining cracking gas (without products of value) has fallen to about 1 $mg/m^3$. The soot present in the process water from the quench, the cooling column and the electrostatic filter has a high hydrocarbon content and is therefore hydrophobic, which causes it to float on the process water. Therefore, this soot-laden process water is passed through what are called open soot channels with surface particulate precipitators. The floating soot components are removed and sent to firing. The process water thus cleaned is subsequently run through an open cooling tower and thus cooled. In the course of this, and during the solid-liquid separation beforehand, a majority of the hydrocarbons bound in liquid and gaseous form in the process water, especially aromatics, alkynes, benzene-toluene-xylene, etc., is emitted into the ambient air together with portions of the process water. Subsequently, the loss of process water which has thus arisen is compensated for by addition and the water circuit is closed in the direction of cooling column and quench.

The emissions of hydrocarbons from the process water from the cooling tower (i.e. in an open process water mode), however, are no longer acceptable under the applicable environmental protection regulations. In the case of a closed process water mode, however, the hydrocarbons would accumulate and lead to polymerization and blockage of the plant, and so a closed process water mode is not an acceptable solution either. A further emission source is that of the open soot channels.

A further process for preparing acetylene and synthesis gas by partial oxidation of hydrocarbons with oxygen is described in US 005824834A. This is a closed water quench process which is optimized for soot volumes and is operated with a lean feed stream, specifically with a feed stream having an oxygen ratio $\lambda<0.31$. However, the process has the disadvantage of a reduced yield of acetylene product of value.

In this process variant, the aqueous quench medium is likewise supplied by means of nozzles the to the cracking gas which is cooled rapidly to about 80-90° C. The soot formed from the gas phase in the firing space is partly precipitated by the quench, a downstream cooling column operated with recirculating water, and a downstream electrostatic filter. The product gas stream containing products of value is removed separately via the cooling column. The process is operated here through selection of the oxygen ratio $\lambda$ ($\lambda>0.31$) such that the soot volume obtained in the cracking gas is so low that solely the discharge of the water of reaction obtained from the incineration can ensure steady-state operation. This, however, reduces the acetylene content in the dry cracking gas by 2 percentage points compared to the above-described process, to about 6% by volume. This enables a closed water quench mode, i.e. one isolated from the environment. The advantage over the above-described process variant is thus the possibility of closed operation without further separation apparatus. The disadvantage is yield losses based on the acetylene product of value and target product.

It was accordingly an object of the invention to provide a process for preparing acetylene and synthesis gas by partial oxidation of hydrocarbons, which combines the advantages of the two processes above, i.e. ensures both a high yield of acetylene product of value and compliance with the applicable environmental protection regulations.

The object is achieved by a process for preparing acetylene and synthesis gas by partial oxidation of hydrocarbons with oxygen, in which a first input stream comprising one or more hydrocarbons and a second input stream comprising oxygen are separately preheated, mixed in a ratio of the mass flow rates of the second input stream to the first input stream corresponding to an oxygen ratio $\lambda$ of less than or equal to 0.31 required for the complete combustion of the one or more hydrocarbons present in the first input stream, supplied via a burner block to a firing space in which the partial oxidation of the hydrocarbons takes place, to obtain a cracking gas which is quenched to 80 to 90° C. downstream of the firing space by injection of an aqueous quench medium, to obtain a process water stream $I_{liq}$ and a product gas stream $I_q$ which is cooled in a cooling column by direct heat exchange with cooling water to obtain a process water stream $II_{liq}$ as the bottom stream, a product gas stream $II_g$ as the top stream and a side stream which is depleted of soot in an electrostatic filter to obtain a process water stream $III_{liq}$ in the electrostatic filter, and process water streams $I_{liq}$, $II_{liq}$ and $III_{liq}$ are combined and passed through soot channels with surface particulate precipitators to obtain a combined process water stream $IV_{liq}$, which comprises subjecting the combined process water stream $IV_{liq}$ to a cleaning operation by partial vaporization in a one-stage flash vessel, the combined process water stream $IV_{liq}$ being vaporized in a proportion of 0.01% by weight to 10% by weight, based on the total weight thereof, to obtain a cleaned process water stream $V_{liq}$, which is recycled into the process.

It has been found that a partial vaporization of the combined process water streams in a one-stage flash vessel results in entrainment of the unwanted dissolved gases, especially polymerizable components, for example higher acetylenes, from the process water streams with the flash vapor into the gas phase, and these gases can be removed from the liquid phase, the combined process water stream, to such an extent that it can be recycled into the process, from which the excess wastewater obtained can also be disposed of.

The vapors of unwanted dissolved gases entrained with the flash vapor can subsequently, for example, after condensation of the water vapor, be incinerated or disposed of in the process in some other way.

It has been shown that, surprisingly, a one-stage flash for partial vaporization of the cleaned process water stream in a proportion of 0.01 to 10% by weight, based on the total weight of the cleaned process water stream, enables sufficient depletion of unwanted dissolved components, such that the process can be conducted in a closed process water circuit.

In a preferred embodiment, the process is conducted with a closed process water circuit. In this process variant, preferably, a substream of the cleaned process water stream is discharged from the process and the remaining substream of the cleaned process water stream is recycled into the process.

In a further preferred process variant, the cleaned process water stream is cooled in an open cooling tower. In this process variant, preferably, the entire cleaned process water stream is recycled into the process.

Preferably, the cleaned process water stream is vaporized in a proportion of 1% by weight to 2% by weight, based on the total weight thereof.

According to the invention, the process for preparing acetylene and synthesis gas is conducted with an oxygen ratio $\lambda$ of less than or equal to 0.31, the oxygen ratio $\lambda$ being understood to mean the ratio of the amount of oxygen actually present in the second input stream to the stoichiometrically necessary amount of oxygen required for the complete combustion of the one or more hydrocarbons present in the first input stream.

In the case of operation with an oxygen ratio $\lambda$ within the above range, a high yield of acetylene product of value is ensured.

The process is independent of the specific form of the reactor system comprising mixing unit, burner block and the quench unit.

The reactor systems typically used are explained in detail hereinafter:

The starting materials, i.e. a gas stream comprising hydrocarbons, especially natural gas, and oxygen, are heated separately, typically up to 600° C. In a mixing unit, the reactants are mixed vigorously and, after flowing through a burner block, are reacted exothermically. The burner block typically consists of a multitude of parallel channels in which the flow rate of the ignitable oxygen/hydrocarbon mixture is higher than the flame speed, in order to prevent the flame from striking through into the mixing unit. The metallic burner block is cooled in order to withstand the thermal stresses. According to the residence time in the mixing unit, there is the risk of pre- and re-ignition due to the limited thermal stability of the mixtures. For this purpose, the term "ignition delay time" or "induction time" is used as the period of time within which an ignitable mixture does not undergo any significant intrinsic thermal change. The induction time depends on the nature of the hydrocarbons used, the mixing state, pressure and temperature. It determines the maximum residence time of the reactants in the mixing unit. Reactants such as hydrogen, liquefied gas or light gasoline, the use of which is particularly desirable due to yield and/or capacity increases in the synthesis process, feature comparatively high reactivity and hence a short induction time.

The acetylene burners being used on the current production scale are notable for the cylindrical geometry of the firing space. The burner block has passage bores preferably in a hexagonal arrangement. In one embodiment, for example, 127 bores of internal diameter 27 mm are arranged hexagonally on a circular base cross section with a diameter of approx. 500 mm. In general, the channel diameters used are about 19 to 27 mm in diameter. The downstream firing space in which the flame of the acetylene-forming partial oxidation reaction is stabilized is typically likewise of cylindrical cross section, is water-cooled and corresponds in terms of appearance to that of a short tube (for example of diameter 180 to 533 mm and length 380 to 450 mm). At the level of the burner block, what is called auxiliary oxygen is supplied to the firing space both in the axial and in the radial direction. This ensures flame stabilization and hence a defined separation of the flame roots and hence of the commencement of reaction from the stopping of the reaction by the quench unit. The overall burner composed of burner block and firing space is suspended from the top by means of a flange into a quench vessel of greater cross section. At the level of the exit plane from the firing space, on the outer circumference thereof, are installed quench nozzles on one or more quench distributor rings, which atomize the quench medium with or without the aid of an atomization medium and inject it virtually at right angles to the main flow direction of the reaction gases leaving the firing space. This direct quench has the task of cooling the reaction mixture extremely rapidly, such that further reactions, i.e. especially the degradation of acetylene formed, are frozen. The range and distribution of the quench jets is ideally such that a very homogeneous temperature distribution is achieved within a very short time.

The present industrial process forms, as well as acetylene, essentially hydrogen, carbon monoxide and soot. The soot particles formed in the flame front can adhere as seeds to the firing space side walls, which then results, under suitable physicochemical conditions, in growth, deposition and caking of coke layers.

These deposits are removed by mechanical cleaning periodically in the region of the firing space walls by means of a poker unit.

The present invention makes use of the fact that, in the above water quench process, a process water stream $I_{liq}$ (a quench water) is obtained at a temperature in the range between 60 and 96° C., preferably with a temperature in the range from approximately 70 to 80° C. The thermal energy present allows sufficient removal of unwanted dissolved gases by partial vaporization into vacuum.

The partial vaporization is preferably effected by one-stage flashing into vacuum.

Further preferably, the partial vaporization by one-stage flashing is effected adiabatically.

In one process variant, the partial vaporization can advantageously be promoted by heat input.

In a further preferred process variant, the soot channels with surface particulate precipitators, through which the combined process water streams I, II and III are passed, are provided with a cover.

Sufficient removal of the dissolved gases can also be achieved by means of a stripping column. For this purpose, the combined process water stream is introduced at the top of the column, and the stripping steam in countercurrent at the bottom of the stripping column. This process step too achieves sufficient depletion of the dissolved gases. The apparatus complexity and hence also the capital costs of the process step are much higher than in the case of the single, inventive flash. Moreover, the internals of the separation stages and distributors which are then necessary have much more of a tendency to be soiled by polymerizing components than the simple structure of a one-stage flash.

The flash vessel preferably has one stage and can be equipped with customary internals, such as structured packings or trays, and also with a demister to prevent droplet entrainment.

Also possible is a multistage flash or a heat input in the bottoms, as in a distillation column, rather than preheating of the feed.

Thus, this process constitutes a very inexpensive means of circulation water cleaning, or wastewater cleaning.

The vacuum can be generated in a manner known in the prior art, for example by means of a steam jet system or a water ring compressor. The offgas can then be treated further within the plant or else supplied to an offgas incineration.

The invention is illustrated in detail hereinafter by a drawing and in working examples.

Figure 2:
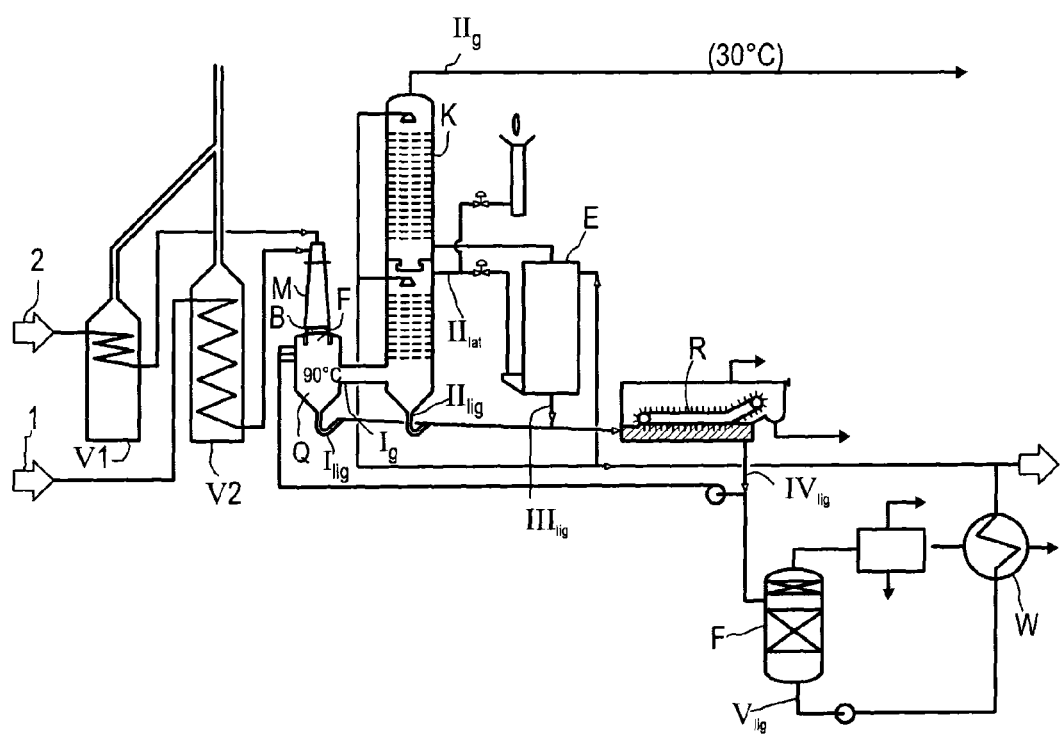

The individual drawings show:

FIG. 1 the schematic diagram of a preferred inventive plant with cooling tower and FIG. 2 the schematic diagram of a further preferred plant for performance of the process according to the invention without a cooling tower.

The plant shown in FIG. 1 is supplied with a gas stream (1) comprising hydrocarbons and a gas stream (2) comprising oxygen, which are preheated separately by means of preheaters V1 and V2, mixed in a mixing unit (M), supplied via a burner block (B) to a firing space (F), and then quenched in a quench region (Q) by injection of an aqueous quench medium to obtain a process water stream $I_{liq}$ and a product gas stream $I_g$.

The product gas stream $I_g$ is cooled in a cooling column (K) by direct heat exchange with cooling water to obtain a process water stream $II_{liq}$ as the bottom stream, a product gas stream $II_g$ as the top stream, and a side stream $II_{lat}$. The side stream $II_{lat}$ is sent to an electrostatic filter (E) and depleted of soot therein to form a process water stream The process water streams $I_{liq}$, $II_{liq}$ and $III_{liq}$ are combined and passed through soot channels (R) with surface particulate precipitators to obtain a combined process water stream $IV_{liq}$. This is supplied to a one-stage flash vessel (F) and partially vaporized therein to obtain a cleaned process water stream $V_{liq}$ which is cooled in a cooling tower (T) and recycled into the process, into the cooling column (K).

The further preferred embodiment shown in FIG. 2 shows a substantially analogous plant, except that a heat exchanger (W) provided in place of the cooling tower (T) is used to cool the combined process water stream $V_{liq}$, which is recycled back into the process, into the cooling column (K).

WORKING EXAMPLES

Comparative Example

Without process water cleaning, the following emissions from the open soot channels and the air output from the cooling tower are obtained in a plant corresponding to the schematic diagram in FIG. 1, specifically for 1 t of acetylene:

| Emissions for open water quench | | | |
|---|---|---|---|
| | Soot channels [kg] | Cooling tower [kg] | total [kg] |
| CO | 0.303 | 0.363 | 0.667 |
| Methane | 5.67E−02 | 8.46E−02 | 0.141 |
| Ethane | 7.63E−03 | 1.21E−02 | 0.020 |
| Ethylene | 6.80E−03 | 2.88E−02 | 0.036 |
| Acetylene | 1.57E−01 | 6.05E+00 | 6.203 |
| Propene | 5.16E−04 | 1.88E−03 | 0.002 |
| Propadiene | 9.83E−04 | 3.58E−03 | 0.005 |
| Propyne | 2.29E−03 | 1.01E−01 | 0.103 |
| Butenyne | 1.65E−03 | 4.58E−02 | 0.047 |
| Butadiyne | 7.39E−03 | 8.91E−01 | 0.898 |
| Benzene | 2.29E−03 | 1.60E−01 | 0.162 |
| Naphthalene | 5.14E−04 | 1.40E−02 | 0.014 |

Working Examples According to the Invention

The cleaning efficiency for the process water is a function of the amount of flash vapor, as shown in the following table:

For this purpose, the process water, proceeding from 84.4° C. and 1013 bar absolute, is flashed to pressures between 200 mbar absolute and 800 mbar absolute. This partly vaporizes the process water in a proportion of 0.0013% by weight to 4.18% by weight. As a function of flash pressure, this results in the following depletions of dissolved gases.

| Depletion by flashing as a function of pressure (open water quench) | | | | |
|---|---|---|---|---|
| Outlet temperature [° C.] | 84.409 | 84.2 | 75.8 | 60 |
| Inlet temperature [° C.] | 84.41 | 84.4 | 84.4 | 84.4 |
| Inlet pressure [bar absolute] | 1.013 | 1.013 | 1.013 | 1.013 |
| Outlet pressure [mbar absolute] | 800 | 600 | 400 | 200 |
| Volume of flash vapor based on feed [%] | 0.0013% | 0.0337% | 1.44% | 4.18% |

| | Depletion | Depletion | Depletion | Depletion |
|---|---|---|---|---|
| CO | 78.1% | 98.9% | 99.98% | 100.00% |
| Methane | 72.7% | 98.5% | 99.97% | 100.00% |
| Ethane | 71.2% | 98.3% | 99.97% | 99.99% |
| Ethylene | 43.1% | 94.4% | 99.90% | 99.98% |
| Acetylene | 7.1% | 60.6% | 98.93% | 99.79% |
| Propene | 47.4% | 95.3% | 99.92% | 99.98% |
| Propadiene | 47.4% | 95.3% | 99.92% | 99.98% |
| Propyne | 6.4% | 57.3% | 98.67% | 99.71% |
| Butenyne | 9.6% | 68.3% | 99.18% | 99.83% |
| Butadiyne | 2.9% | 32.9% | 95.97% | 98.91% |
| Benzene | 4.2% | 45.8% | 97.93% | 99.52% |
| Naphthalene | 10.5% | 71.9% | 99.30% | 99.85% |

It is clearly shown that the depletion depends strongly on the flash pressure.

If an inventive, for example one-stage, flash of the process water is effected upstream of the cooling tower, this results only in the following emissions to the environment:

The process water enters the one-stage flash stage at 84.4° C. and is flashed to 400 mbar absolute.

This cools the stream from 84.4° C. to 75.8° C. and forms 1.44% flash vapor based on the feed.

The table also states the depletion by the cleaning step in percent.

| Emissions for open water quench with flash | | |
|---|---|---|
| | Cooling tower Flow rate kg/t Ac | Depletion in % |
| CO | 1.20E−04 | 99.9820% |
| Methane | 3.53E−05 | 99.9750% |
| Ethane | 5.39E−06 | 99.9726% |
| Ethylene | 3.55E−05 | 99.9002% |
| Acetylene | 6.67E−02 | 98.9253% |
| Propene | 1.99E−06 | 99.9172% |
| Propadiene | 3.78E−06 | 99.9172% |
| Propyne | 1.37E−03 | 98.6727% |
| Butenyne | 3.90E−04 | 99.1785% |
| Butadiyne | 3.62E−02 | 95.9707% |
| Benzene | 3.36E−03 | 97.9296% |
| Naphthalene | 1.01E−04 | 99.3007% |

Due to the high depletion rate, the cooling tower can be replaced by a closed heat exchanger without intolerable accumulations of polymerizable components, especially of higher acetylenes, in the process.

| Secondary components in the process water | | |
|---|---|---|
| | closed water quench without flash [ppm by wt.] | closed water quench with flash [ppm by wt.] |
| CO | 1.846 | 0.001 |
| Methane | 0.430 | 0.000 |
| Ethane | 0.061 | 0.000 |
| Ethylene | 0.146 | 0.000 |
| Acetylene | 30.537 | 0.333 |
| Propene | 0.010 | 0.000 |
| Propadiene | 0.018 | 0.000 |
| Propyne | 0.514 | 0.007 |
| Butenyne | 0.233 | 0.002 |
| Butadiyne | 4.606 | 0.182 |
| Benzene | 0.018 | 0.017 |
| Naphthalene | 0.071 | 0.001 |

The invention claimed is:

1. A process for preparing acetylene and synthesis gas by partial oxidation of hydrocarbons with oxygen, the process comprising:
   separately preheating a first input stream comprising a hydrocarbon and a second input stream comprising oxygen,
   mixing the first input stream and the second input stream in a ratio of mass flow rates of the second input stream to the first input stream corresponding to an oxygen ratio λ of less than or equal to 0.31, wherein the oxygen ratio λ is a ratio of an amount of oxygen actually present in the second input stream to a stochiometrically necessary amount of oxygen required for complete combustion of the hydrocarbon present in the first input stream;
   supplying the first input stream and the second input stream via a burner block to a firing space in which the partial oxidation of the hydrocarbon takes place to obtain a cracking gas;
   quenching the cracking gas to of from 80 to 90 degrees Celsius downstream of the firing space by injecting an aqueous quench medium, to obtain a process water stream $I_{liq}$ and a product gas stream $I_g$;
   cooling the product gas stream $I_g$ in a cooling column by direct heat exchange with cooling water to obtain a process water stream $II_{liq}$ as a bottom stream, a product gas stream $II_g$ as a top stream and a side stream;
   depleting soot from the side stream in an electrostatic filter to obtain a process water stream $III_{liq}$ in the electrostatic filter;
   combining process water streams $I_{liq}$, $II_{liq}$ and $III_{liq}$ and passing through soot channels comprising surface particulate precipitators to obtain a combined process water stream $IV_{liq}$;
   subjecting the combined process water stream $IV_{liq}$ to a cleaning operation by partial vaporization in a one-stage flash vessel, wherein the combined process water stream $IV_{liq}$ is vaporized in a proportion of from 0.01% by weight to 10% by weight, based on a total weight thereof, to obtain a cleaned process water stream $V_{liq}$; and
   recycling the cleaned process water stream $V_{liq}$ into the process.

2. The process according to claim 1, comprising fully recycling the cleaned process water stream $V_{liq}$ into the process.

3. The process according to claim 2, wherein the combined process water stream $IV_{liq}$ is vaporized in a proportion of from 1% by weight to 2% by weight, based on the total weight thereof.

4. The process according to claim 2, wherein the partial vaporization is effected by flashing into a vacuum.

5. The process according to claim 2, wherein the partial vaporization by flashing is effected adiabatically.

6. The process according to claim 2, wherein the partial vaporization is promoted by heat input.

7. The process according to claim 1, comprising disposing a substream of the cleaned process water stream $V_{liq}$ as wastewater, and recycling a remaining substream of the cleaned process water stream $V_{liq}$ into the process.

8. The process according to claim 7, wherein the combined process water stream $IV_{liq}$ is vaporized in a proportion of from 1% by weight to 2% by weight, based on the total weight thereof.

9. The process according to claim 7, wherein the partial vaporization is effected by flashing into a vacuum.

10. The process according to claim 7, wherein the partial vaporization by flashing is effected adiabatically.

11. The process according to claim 7, wherein the partial vaporization is promoted by heat input.

12. The process according to claim 1, wherein the combined process water stream $IV_{liq}$ is vaporized in a proportion of from 1% by weight to 2% by weight, based on the total weight thereof.

13. The process according to claim 12, wherein the partial vaporization is effected by flashing into a vacuum of from 50 to 900 mbar a.

14. The process according to claim 12, wherein the partial vaporization is effected by flashing into a vacuum of from 200 to 600 mbar a.

15. The process according to claim 12, wherein the partial vaporization is effected by flashing into a vacuum.

16. The process according to claim 1, wherein the partial vaporization is effected by flashing into a vacuum.

17. The process according to claim 1, wherein the partial vaporization by flashing is effected adiabatically.

18. The process according to claim 1, wherein the partial vaporization is promoted by heat input.

19. The process according to claim 18, wherein the heat input is effected by direct steam injection.

20. The process according to claim 1, wherein the soot channels further comprise a cover.

* * * * *